United States Patent [19]

Neri et al.

[11] Patent Number: 4,564,691
[45] Date of Patent: Jan. 14, 1986

[54] PROCESS FOR PREPARING SUBSTITUTED 2,3-DIHYDROBENZOFURAN

[75] Inventors: Carlo Neri; Villiam Giroldini; Antonio Rinaldi, all of Milan; Mario Traversoni, Bergamo; Mario Clerici, Milan, all of Italy

[73] Assignee: Enichimica Secondaria S.p.A., Palermo, Italy

[21] Appl. No.: 602,215

[22] Filed: Apr. 19, 1984

[30] Foreign Application Priority Data

Apr. 22, 1983 [IT] Italy ................ 20737 A/83
Apr. 22, 1983 [IT] Italy ................ 20740 A/83

[51] Int. Cl.$^4$ .................. C07D 307/86; C07D 307/79
[52] U.S. Cl. ........................... 549/462; 568/723; 568/726; 568/727
[58] Field of Search ........................ 549/462

[56] References Cited

PUBLICATIONS von Braun et al., Chem. Abstracts, vol. 23, (1929), p. 4687–4690.

Primary Examiner—Henry R. Jiles
Assistant Examiner—Bernard I. Dentz
Attorney, Agent, or Firm—Hedman, Gibson, Costigan & Hoare

[57] ABSTRACT

A process is provided for preparing a substituted 2,3-dihydrobenzofuran of the general formula

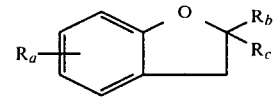

in which $R_a$ is hydrogen, halogen, alkyl, straight or branched having from 1 to 4 carbon atoms, aryl, alkaryl, —OH, —OR$_3$, —N(R$_d$)$_2$, where R$_3$ and R$_d$ are alkyl, straight or branched having from 1 to 4 carbon atoms; $R_b$ is alkyl, straight or branched, having from 1 to 6 carbon atoms, aryl, alkaryl; and $R_c$ is hydrogen or the same as $R_b$, by the rearrangement of a 1,1-bis(2-hydroxybenzene) alkyl and/or aryl-ethane, in the presence of catalytic amounts of a mineral acid or organic acid such as phosphoric, sulfuric or p-toluenesulfonic, at elevated temperatures from 180° to 250° C., and withdrawing the resulting products from the reaction mixture as they are formed. The starting 1,1-bis(2-hydroxybenzene) alkyl and/or aryl-ethane compounds may be obtained by the catalyzed reaction of a substituted biphenol with an aldehyde. The substituted 2,3-dihydrobenzofurans are useful in the manufacture of pesticides.

4 Claims, No Drawings

PROCESS FOR PREPARING SUBSTITUTED 2,3-DIHYDROBENZOFURAN

FIELD OF THE INVENTION

This invention relates to a process for the preparation of substituted 2,3-dihydrobenzofuran compounds.

BACKGROUND OF THE INVENTION

Substituted benzofurans are appreciable intermediates, which are useful, for example, in the synthesis of pesticides, such as CARBOFURAN, i.e. 2,3-dihydro-2,2-dimethyl-7-benzofuranyl -methyl-carbamate).

Many processes are known in the art for the preparation of substituted 2,3-dihydrobenzofurans, such as reported, for example, by Ahmed Mustafa in "The Chemistry of Heterocyclic Compounds", vol. 29, pages 143 and seqq.

One of such processes is based on the condensation of unsaturated alcohols with phenols or cresols, as obtained by heating in the presence of a mixture of sulphuric and acetic acids, followed by the thermal decomposition of the polymeric reaction product thus obtained. Another conventional procedure is based on the cyclization of O-allylphenols and their attendant methyl esters, in the presence of catalysts such as pyridinium chloride, potassium bisulphate and mixtures of acids, such as the mixtures of hydrobromic acid/acetic acid, and sulphuric acid/hydrochloric acid. According to another conventional process alkyl bromides or chlorides are reacted with phenols under reflux conditions in the presence of potassium carbonate, the subsequent step being the rearrangement of the as-obtained allylphenyl ethers and the cyclization with hydrogen bromide, to obtain the alkyl-substituted 2,3-dihydrobenzofurans.

Still other procedures can be adopted for preparing the compounds in question, such as for example:

condensation reaction of conjugated dienes with phenols, in the presence of acidic catalysts;

reaction of substituted styrene oxide with phenoxide ions in an acidic environment, and alkenylation reaction of phenols with substituted acetylenes, followed by the cyclization reaction of the resultant reaction product.

These conventional approaches are not entirely satisfactory from one or more of the following standpoints: availability and economical acceptability of the raw materials, conversion and selectivity of the reactions which convert such raw materials and simplicity of the conversion process in question.

It has now been found that the 1,1-bis(2-hydroxybenzene) alkyl and/or aryl-ethane compounds are easily subjected to rearrangement under the action of organic or mineral acidic compounds and such rearrangement reaction runs in a rapid and selective way towards the formation of the corresponding substituted 2,3-dihydrobenzofuran compounds.

In their turn, the 1,1-bis(2-hydroxybenzene) alkyl and/or aryl ethane compounds are obtained starting from substituted phenols and aldehydes under the influence of specially provided catalysts.

Now, therefore, according to a first aspect of the present invention, substituted 2,3-dihydrobenzofuran compounds are prepared by a simple procedure which provides high conversions and selectivities, starting from raw materials of a comparatively moderate cost which are very readily availble on the market.

Consistently with the foregoing, substituted 2,3-dihydrobenzofuran compounds are prepared according to the present invention, and have the general formula:

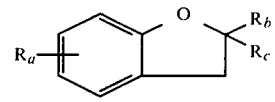

wherein:

$R_a$ is hydrogen, a halogen, or an alkyl radical, straight lined or branched, containing from 1 to 4 carbon atoms, aryl, alkaryl, —OH, —OR$_3$, —N(R$_d$)$_2$ (R$_d$ and R$_3$ being, in its turn, a straight lined or branched alkyl radical having from 1 to 4 carbon atoms);

$R_b$ is a straight lined or a branched alkyl radical having from 1 to 6 carbon atoms, an aryl or an alkaryl; $R_c$ is hydrogen or has the same meaning as $R_b$, by rearrangement of 1,1-bis(2-hydroxybenzene)alkyl- and/or aryl ethane, which are defined by the general formula:

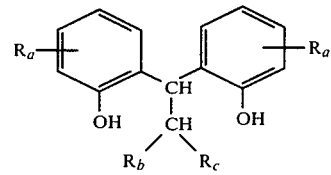

wherein $R_a$, $R_b$ and $R_c$ have the meanings specified hereinabove, working in the presence of catalytic amounts of at least one organic or mineral acidic compound, at a high temperature and removing from the reaction mass the products of the rearrangement reaction as they are being formed.

The rearrangement reaction according to the present invention can be summed up by the following pattern:

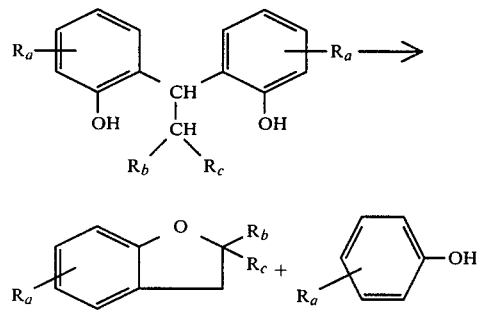

The 1,1-bis(2-hydroxybenzene)alkyl- and/or aryl ethane compounds which are the starting materials for the process of the present invention, can be prepared by reacting a phenol (such as for example catechol and 4-tert.butyl-catechol) with an aldehyde which has at least three carbon atoms in its molecule (examples are isobutyraldehyde and n.propionaldehyde) under the influence of catalysts of the type of oxides, hydroxides, alcoholates and carboxylates of elements such as sodium, calcium, magnesium, zinc and manganese, in the presence, or not, of a liquid organic and inert (i.e. nonreactive) solvent and removing the water as it is being formed as a reaction byproduct.

The process in question is carried out by a step sequence to be derived from the particular case, which is an additional subject matter of the present invention, and relates to the preparation of 1,1-bis(2,3-dihydroxybenzene) alkyl- and/or aryl methanes, that is, a novel class of compounds which are useful as antioxidants or as intermediates for the synthesis of phytopharmacological products.

Known in the art is the preparation of variously substituted diarylmethanes by reacting methylene chloride with substituted benzenes, in the presence of alkylation catalysts (for example aluminum trichloride), or by reacting an aryl chloride with aromatic hydrocarbons, such as described for example by Friedel, Crafts in Bull. Soc. Chim. (2), 41, page 324 (1884), Hartman, Philips in Organic Synthesis, 14, 34 (1934), L. F. Fieser, Experiments in Organic Chemistry, Boston, 1955, page 157.

Whenever the alkylation reaction involves monohydric phenols, a mixture of reaction products is obtained, in which the aromatic rings are connected to each other in the ortho and the para positions relative to the phenolic hydroxyl. In the case of vicinal bihydric phenols, the orientation effect being such as to preferentially bring about an alkylation in the para position.

The present invention is essentially based on the unexpected circumstance according to which the vicinal bihydric phenols, be they substituted or unsubstituted, react with the aldehydes to selectively give alkylation products in the ortho position, whenever the reaction is carried out in the presence of catalytic amounts of compounds having a catalytic activity, to be defined in more detail hereinafter.

According to these principles, and according to the present invention, 1,1-bis(2,3-dihydroxybenzene)alkyl- or aryl-methanes are prepared, which can be defined by the following general formula:

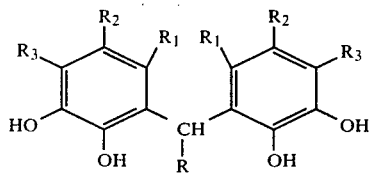

wherein R is a straight lined or branched alkyl radical having from 1 to 20 carbon atoms, or an aryl radical; $R_1$, $R_2$ and $R_3$ are equal to or different from each other and represent: H, a halogen, or a straight lined or a branched alkyl radical having from 1 to 4 carbon atoms, an aryl radical, an alkaryl radical, —OH, —OH$_4$ or —N(R$_4$)$_2$, $R_4$ being a straight lined or a branched alkyl radical having from 1 to 4 carbon atoms, by the particular reaction of a biphenol defined by the following general formula:

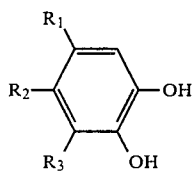

with an aldehyde which can be defined by the general formula

R-CHO wherein R, $R_1$, $R_2$ and $R_3$ have the same meanings as explained above, working at a temperature of from 80° C. to 180° C. and in the presence of catalytic amounts of at least one compound selected from the group consisting of the oxides, the hydroxides, the alcoholates and the carboxylates of the metals belonging to the groups IA, IIA, IIB and VIIB of the Periodic System of the Elements, in the optional presence of a liquid and inert (nonreactive) organic solvent and recovering the expected product from the reaction mixture thus obtained.

Typical representatives of 1,1-bis(2,3-dihydroxybenzene) alkyl- or aryl-methanes which can be obtained by the process according to the present invention, are those corresponding to the general formula reported in the foregoing, wherein R is the ethyl or the isopropyl radical, and $R_1$ and $R_2$, and $R_3$ are hydrogen, or, as an alternative, $R_1$ and $R_3$ are hydrogen and $R_2$ is the tert.butyl radical, such as, for example:

1,1-bis(2,3-dihydroxybenzene)isopropyl methane;
1,1-bis(2,3-dihydroxy-5-tert.butylbenzene)isopropyl methane; and
1,1-bis(2,3-dihydroxy-5-tert.butylbenzene)ethyl methane.

Examples of biphenols useful for the process according to the present invention are catechol and 4-tert.butylcatechol.

Examples of aldehydes which are useful for the process according to the present invention are the compounds according to the general formula reported above, in which R is an ethyl, propyl, isopropyl, butyl, isobutyl and phenyl radical, such as isobutyraldehyde and the n.propionaldehyde.

The reaction generally adopts molar ratios of the biphenol to the aldehyde of from 0.4:1 to 1.6:1, the preferred range of values being from 0.6:1 to 1.6:1.

The catalysts which are useful for the purposes of the present invention are members selected from the group consisting of the oxides, the hydroxides, the alcoholates and the carboxylates of the metals belonging to the Groups IA, IIA, IIB and VIIB of the Periodic System of the Elements. Particularly useful are the compounds of sodium, calcium, magnesium, zinc and manganese. Especially preferred are calcium oxide, sodium methylate, and zinc acetate.

These compounds unfold their catalytic activity in concentrations which vary from 0.5% to 5% by weight with respect to the biphenol concerned, the preferred range being from 0.7% to 0.8%, still on a weight basis.

The reaction temperature may generally vary from 80° C. to 180° C., the preferred range being from 110° C. to 160° C.

According to a preferred embodiment, the water which is formed as a reaction byproduct is removed from the reaction mixture as it is being formed. Thus, the pressure at which the reaction is carried out is adjusted, as a function of the preselected reaction temperature, so as to carry out the water removal intended. The reaction can be carried out in the presence of a liquid and inert (nonreactive) organic solvent consistently with the working conditions. Examples of organic solvents which are useful for the intended purpose are the hydrocarbons, the alcohols and the ethers.

According to a preferred embodiment, the water, which is a reaction byproduct, is continually withdrawn by azeotropic distillation with the organic solvent as used as a reaction medium.

The reaction times are varied as a function of the starting materials and of the temperature which is selected for the reaction. From a quite practical standpoint, the reaction is considered as having been completed as the evolution of water ceases in the embodiment in which water is continually withdrawn from the reaction mixture.

The raw reaction mixture thus obtained is then subjected to the conventional treatments for separating the unreacted reactants from the reaction products proper.

Usually, the procedure is to distill off the solvent, if any, and the unreacted aldehyde. The distillation residue is then subjected to fractional crystallization.

Reverting now to the rearrangement reaction, according to the present invention, in one case the 1,1-bis(2-hydroxybenzene) alkyl- and/or aryl ethane compounds in their state of purity or substantially pure, or, as an alternative, the raw reaction mixture as such can be used, which contains the 1,-bis(2-hydroxybenzene) alkyl and or aryl ethane, as obtained by the process outlined above.

Moreover, said 1,1-bis(2-hydroxybenzene) alky and/or aryl ethane compounds may contain one or more $R_a$ groups, equal to or different from each other, in their very benzene ring itself.

Typical examples of compounds which are useful as starting materials in the process according to the present invention are those corresponding to the general formula reported hereinabove, in which $R_b$ and $R_c$ are methyl groups and which contain an $R_a$ group in the position 3 and/or 5 and consisting of methyl, tert.butyl or hydroxyl, such as, for instance, 1,1-bis(2,3-dihydroxybenzene)dimethyl ethane, 1,1-bis(2,3-dihydroxy-5-tert-.butylbenzene)dimethyl ethane and 1,1-bis(2-hydroxy-3,5-dimethylbenzene)dimethyl ethane.

The catalysts which can be used for the rearrangement reaction consists of acids, or, in general, of substances of an acidic nature, both organic and mineral, such as, for example, the phosphoric, sulphuric and para-toluenesulphonic acids, potassium bisulphate, the acidic zeolites and the acidic aluminas.

Among all these catalysts, the preferred one is the phosphoric acid ($H_3PO_4$) and the aqueous phosphoric acid having a concentration of from 50% to 100%, on account of its outstanding stability under the reaction conditions.

The catalysts are generally used in the amount of from 1 to 10 parts by weight for 100 parts by weight of the compound, 1,1-bis(2-hydroxybenzene)alkyl and/or aryl ethane which has been subjected to the rearrangement reaction. With amounts below 1 part by weight, the catalytic action is unfolded inadequately, whereas no special advantages are obtained with amounts above 10 parts by weight.

The preferred amounts for the catalysts are in the range of from 2 to 5 parts by weight for 100 parts by weight of the 1,1-bis(2-hydroxybenzene)alkyl and/or aryl ethane subjected to rearrangement.

The reaction temperatures are generally comprised in the range of from 180° C. to 250° C., as a function of the particular compound which is subjected to rearrangement, the preferred temperature range being of from 200° C. to 240° C.

According to an important aspect of the process according to the present invention the products of the rearrangement of the 1,1-bis(2-hydroxybenzene)alkyl and/or aryl ethane are removed from the reaction mass in the vapor form, continually, as they are being formed. Thus, the reaction is carried out under a reduced pressure, so as to make the removal quite possible. Pressure values which are useful for the intended purpose are in the range of from 5 mmHg to 30 mmHg and this in view of the temperature range aforementioned.

The reaction products which have been thus obtained are now condensed and subsequently subjected to the conventional separation and purification stages.

Typical examples of substituted 2,3-dihydrobenzofuran compounds as obtained by the process according to the present invention, are those corresponding to the general formula reported hereinabove in which $R_b$ and $R_c$ are a methyl radical, and which contain a methyl, tert.butyl or hydroxyl group in the 5 position and/or in the 7 position, such as, for instance: 7-benzofuranol-2,3-dihydro-2,2-dimethyl 5-tert.butyl-7-benzofuranol-2,3-dihydro-2,3-dimethyl, and 5,7-dimethylbenzofuran -2,3-dihydro-2,2-dimethyl.

The experimental examples reported hereinafter are illustrations of the invention and not limitations.

EXAMPLE 1

Preparation of 1,1-bis(2,3-dihydroxybenzene) dimethyl ethane

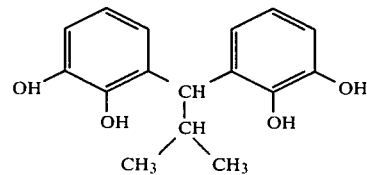

A 250-ml flask, equipped with magnetic bar stirrer and Marcusson separator is charged with 110 g (1 mol) of catechol, 56 mls (0.62 mol) of isobutyraldehyde, 0.8 g (0.014 mol) of calcium oxide (CaO) and 30 mls of toluene. The mixture is brought to a boil (about 120° C.) under atmospherical pressures and water is azeotropically removed as it is being formed as a reaction by-product. The reaction is discontinued after approximately 8 hours, when about 10 mls of water have been withdrawn.

Preparation of 7-benzofuranol -2,3-dihydro-2,2-dimethyl

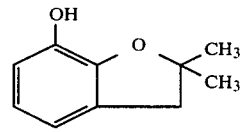

To the reaction mixture, as obtained as described hereinbefore and containing 1,1-bis(2,3-dihydroxybenzene) dimethyl ethane as the principal reaction product, there are added 7 g of aqueous phosphoric acid ($H_3PO_4$) having a density of 1.7 g/ml, corresponding to a concentration of 85%.

The reaction mass is heated by an external bath maintained at 220° C.-240° C. and the reaction products are distilled off, as they are being formed, under a pressure of 20 mmHg. During a time of about 3 hours, 63.5 g of catechol are distilled, together with 35 g of the expected product, 7-benzofuranol -2,3-dihydro-2,2-dimethyl, having a boiling point of 120° C. at 20 mmHg. The selectivity of the expected product is thus equal to about 50% relative to the starting catechol.

EXAMPLE 2

Preparation of 5-tert.butyl-7-benzofuranol -2,3-dihydro-2,2-dimethyl

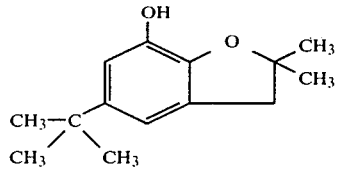

A 100-ml flask, equipped with a magnetic bar stirrer, is charged with 31 g (0.08 mol) of 1,1-bis(2,3-dihydroxy-5-tert.butylbenzene) dimethyl ethane and 0.6 g of aqueous phosphoric acid ($H_3PO_4$) having a density of 1.7 g/ml, corresponding to a concentration of 85%. The mass is heated by an external bath maintained at 205° C. and the reaction products are distilled off, as they are being formed, under a pressure of 5 mmHg. During a period of about 3 hours there are distilled 6.22 g (0.0375 mol) of 4-tert.butyl catechol, and 15.4 g (0.07mol) of 5-tert.butyl-7-benzofuranol-2,3-dihydro-2,2-dimethyl, having a boiling point of 130° C. at 5 mmHg.

EXAMPLE 3

Preparation of 5,7-dimethylbenzofuran-2,3-dihydro-2,2-dimethyl

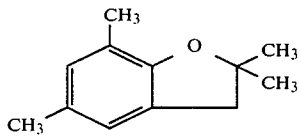

A 100-ml flask, equipped with a magnetic bar stirrer, is charged with 41 g (0.137 mol) of 1,1-bis(2-hydroxy-3,5-dimethylbenzene) dimethyl ethane and 2 g of aqueous phosphoric acid ($H_3PO_4$) having a density of 1.7 g/ml, corresponding to a concentration of 85%.

The reaction mass is heated in a kettle maintained at 240° C. and the reaction products are distilled off as they are being formed, under a pressure of 25 mmHg.

During a period of 3 hours, there are distilled 15.5 g (0.127 mol) of 2,4-dimethylphenol, 5.8 g (0.033 mol) of 2,4dimethylisobutylphenol and 16.5 g (0.094 mol) of the expected product, 5,7-dimethylbenzofuran-2,3-dihydro-2,2-dimethyl, which has a boiling point of 113° C. at 20 mmHg. This isobutylene derivative, by the action of hot acids, is cyclized to give the corresponding benzofuran.

All the reaction products as obtained by the experimental Examples reported above have been identified by analytical determinations such as gas-liquid chromatography, gas-mass (gas-chromatography coupled with mass spectrometry) and NMR.

EXAMPLE 4

Preparation of 1,1-bis(2,3-dihydroxybenzene) isopropyl-methane

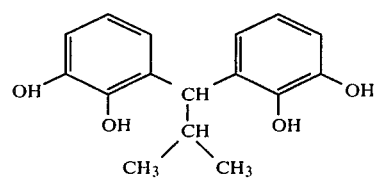

A 250-ml flask, equipped with magnetic bar stirrer and Marcusson separator, is charged with 110 g (1 mol) of catechol, 56 mls (0.62 mol) of isobutyraldehyde, 0.8 g (0.014 mol) of calcium oxide (CaO) and 40 mls of toluene. The mixture is brought to a boil (about 120° C.) under the environmental pressure and water is azeotropically removed as it is being formed as a reaction byproduct. The reaction is discontinued after about 8 hours, when about 10 mls of water have been removed. The raw reaction mixture thus obtained contains, as its principal reaction product, the 1,1-bis(2,3-dihydroxybenzene)isopropylmethane, which has been formed with a yield equal to about 80% of the catechol feedstock.

The density of the latter product is established by the following analytical determinations:
  HPLC (High Pressure Liquid Chromatography)
  Gas-Mass (Gaschromatography coupled with mass spectrometry) of the relative silanized derivative, and
  Thin-Layer Chromatography and Thermal Rearrangement, catalyzed by acids, to 7-benzofuranol -2,3-dihydro-2,2-dimethyl.

EXAMPLE 5

Preparation of 1,1-bis(2,3-dihydroxy-4-tert.butylbenzene)-isopropyl methane

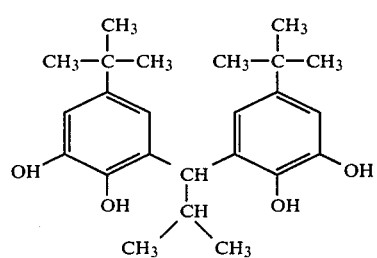

A 500-ml flask, equipped with a magnetic bar stirrer and a Marcusson separator, is charged with 249 g (1.5 mol) of 4-tert.butylcatechol, 170 mls (1.9 mol) of isobutyraldehyde, 2 g (0.035 mol) of calcium oxide (CaO) and 200 mls of toluene. The mixture is brought to a boil (about 120° C.) under the environmental pressure and water is removed azeotropically as it is being formed as a reaction byproduct. The reaction is discontinued after about 8 hours, when about 16.5 mls of water have been removed. Toluene and unreacted isobutyraldehyde are the distilled off. The raw reaction mixture thus obtained shows, when analyzed, the following composition: 4-tert.butylcatechol: 0.217 mol 4-tert.butyl-6-isobutenylcatechol: 0.516 mol, and 1,1-bis(2,3-dihydroxy-5-tert-.butylbenzene)-isopropyl methane: 0.38 mol.

The last named product is isolated in pure form by fractional crystallization and exhibits a melting point of 177° C. Its identity is confirmed by NMR analysis, mass-spectrometry and IR.

EXAMPLE 6

Preparation of 1,1-bis(2,3-dihydroxy-5-tert.butylbenzene) ethyl-methane

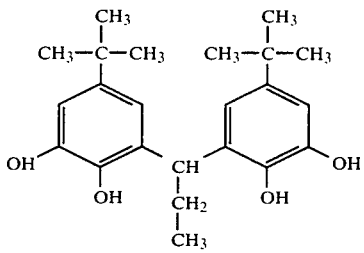

A 250-ml flask, equipped with a magnetic bar stirrer and a Marcusson separator, is charged with 83 g (0.5 mol) of 4-tert.butylcatechol, 60 mls (0.83 mol) of n.propionaldehyde, 0.6 g (0.01 mol) of calcium oxide (CaO) and 40 mls of toluene. The mixture is brought to a boil (about 120° C.) under the environmental pressure and water is azeotropically removed, as it is being formed as a reaction byproduct. The reaction is discontinued after about 8 hours, when about 8 mls of water have been removed.

In the raw reaction mixture thus obtained the following compounds are identified: 4-tert.butylcatechol: 0.05 mol 1,1-bis(2,3-dihydroxy-5-tert.butylbenzene) ethyl methane: 0.15 mol.

The last named product is isolated by fractional crystallization and its identity is confirmed by NMR analysis, mass spectrometry and IR.

We claim:

1. A process for the preparation of a substituted 2,3-dihydroxybenzofuran defined by the formula:

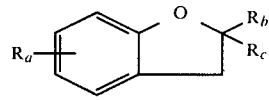

wherein $R_a$ is selected from the group consisting of hydrogen, halogen, a straight lined or branched alkyl radical having from 1 to 4 carbon atoms, aryl, alkaryl, —OH, —OR$_3$, and -N(R$_d$)$_2$, R$_d$ and R$_3$ being a straight lined or branched alkyl radical having from 1 to 4 carbon atoms; R$_b$ is selected from the group consisting of a straight lined or a branched alkyl radical having from 1 to 6 carbon atoms, an aryl and an alkaryl; R$_c$ is hydrogen or has the same meaning as R$_b$, comprising subjecting a starting compound defined by the general formula:

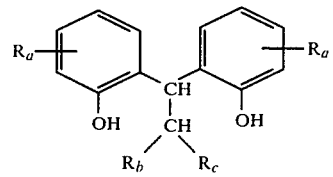

wherein $R_a$, $R_b$ and $R_c$ have the meanings explained above to a rearrangement reaction in the presence of a catalytic amount of at least one acid compound, at an elevated temperature, and removing from the reaction mass the products of the rearrangement reaction as they are formed.

2. A process according to claim 1, wherein the catalyst is a member selected from the group consisting of phosphoric acid, sulphuric acid, p-toluenesulphonic acid, potassium bisulphate, acidic zeolites and acidic alumina.

3. A process according to claim 1, wherein the catalyst is used in an amount of from 1 to 10 parts by weight for 100 parts by weight of the starting compound.

4. A process according to claim 1, wherein the reaction temperature is from 180° C. to 250° C.

* * * * *